(12) United States Patent
Garrett et al.

(10) Patent No.: US 10,143,413 B2
(45) Date of Patent: Dec. 4, 2018

(54) CATHETER INSERTION DEVICE WITH BLOOD ANALYZER

(71) Applicant: KURIN, INC., San Diego, CA (US)

(72) Inventors: Chad Garrett, Carlsbad, CA (US); John W. Simpson, Irvine, CA (US)

(73) Assignee: KURIN, INC., San Diego, CA (US)

( * ) Notice: Subject to any disclaimer, the term of this patent is extended or adjusted under 35 U.S.C. 154(b) by 596 days.

(21) Appl. No.: 14/516,249

(22) Filed: Oct. 16, 2014

(65) Prior Publication Data
US 2015/0359473 A1  Dec. 17, 2015

(51) Int. Cl.
*A61B 5/157* (2006.01)
*A61B 5/153* (2006.01)
*A61M 25/06* (2006.01)
*A61B 5/15* (2006.01)

(52) U.S. Cl.
CPC .......... *A61B 5/157* (2013.01); *A61B 5/15003* (2013.01); *A61B 5/1535* (2013.01); *A61B 5/150992* (2013.01); *A61M 25/0693* (2013.01)

(58) Field of Classification Search
CPC ............ A61B 5/14532; A61B 5/14546; A61B 5/1486; A61B 5/14539; A61B 5/0031
See application file for complete search history.

(56) References Cited

U.S. PATENT DOCUMENTS

| | | | | |
|---|---|---|---|---|
| 5,432,084 A | * | 7/1995 | Brubaker | G01N 33/4905 422/404 |
| 2001/0044615 A1 | * | 11/2001 | Amano | A61B 5/15003 604/413 |
| 2003/0082074 A1 | * | 5/2003 | Jurik | G01N 33/523 422/423 |
| 2003/0185707 A1 | * | 10/2003 | Iwaki | G01N 21/8483 422/82.05 |
| 2004/0116830 A1 | * | 6/2004 | Trudeau | A61B 5/14532 600/584 |
| 2013/0158506 A1 | * | 6/2013 | Harris | A61B 17/3415 604/506 |

\* cited by examiner

*Primary Examiner* — Eric Winakur

(57) ABSTRACT

A device and method yielding a blood analysis employable in combination with an introducer for a catheter for a concurrent testing of blood from the introducer flash chamber during placement of a venous catheter. The device employs a colorimetric blood analysis to provide the user a visually discernable alert to the results of tested blood concurrent with the placement of the catheter with the introducer.

10 Claims, 2 Drawing Sheets

CATHETER INSERTION DEVICE WITH BLOOD ANALYZER

This application claims the benefit of U.S. Provisional Patent Application Ser. No. 62/011,741 filed on Jun. 7, 2014, and is incorporated herein in its entirety by this reference thereto.

FIELD OF THE INVENTION

The present device relates to catheter insertion devices and blood testing equipment. More particularly, the disclosed device, and method relates to a catheter assembly adapted for engagement with a needle which includes a visually discernable signaling component configured to visually change appearance upon communication thereto of blood having a determined level of substance therein. The visual change provides the user an alert to blood levels of certain components during the provision of emergency services which may be of immediate concern, such as blood sugar levels or alcohol levels.

BACKGROUND OF THE INVENTION

Intravenous catheters for the infusion of fluids into the peripheral veins of a patient are one of the most common devices employed in hospitals and especially by Emergency Service Technicians responding to a scene where the patient requires emergency medical care. In providing medical services to a patient, emergency healthcare providers frequently are required to insert a catheter into the patient on arrival or before transport. Hospital medical personnel have the same requirements in tending to a patient.

The insertion of a catheter allows the medical provider to provide medications, fluids, blood, and blood plasma directly into the circulatory system of the patient. In the case of emergency responders, the insertion of a catheter also provides line access for subsequent hospital personnel, to allow for immediate care upon arrival at a hospital.

During insertion of a catheter into a patient's blood vessel, a catheter insertion device or introducer, is engaged with a catheter assembly. The introducer having a hollow needle, is inserted to puncture the intended blood vessel of the patient. As a signal to the medical provider that the needle successfully communicated into the blood vessel, blood travels through the length of the hollow needle and exits into a visually discernable flash chamber, in a surge commonly called a flashback.

The typically transparent flashback chamber of an introducer thereby serves as a visual indication of successful entry into the blood vessel. Concurrently, the flash communication of blood into the chamber alerts the medical provider that further insertion of the needle of the introducer, may cause the needle to pierce the blood vessel's opposing wall. Flash chambers in catheter introducers used to insert catheter assemblies are sized such that they fill with blood within a very short time period to allow the medical provider to verify the needle has reached its mark.

Catheters may be produced in two general forms, though-the-needle catheters, in which a catheter is threaded through the needle cannula of the introducer and into the vein of a patient, and over-the-needle catheter assemblies, in which the needle of the introducer and coaxial outer catheter, are inserted into the vein or artery concurrently, whereafter the needle is withdrawn through the catheter upon verification of blood communicated to the flash chamber of proper positioning.

In typical catheter insertion assemblies, for use by emergency personnel, the user removes and disposes the contaminated needle and introducer after a proper catheter assembly positioning.

Alternatively, a tab on the needle guard is employed to allow the user to simultaneously thread the catheter tube into the blood vessel and retract the needle of the introducer from the catheter tube. The needle guard then slides and locks into place to protect the user and others from the contamination.

Emergency responders, on arrival to an incident, conventionally check several vital signs before and during transport to a hospital. The same occurs in a hospital emergency room when a patient arrives who has not been transported by an ambulance.

During this process the emergency provider begins to diagnose or treat the patient for perceived medical problems to save vital time for the emergency room doctors and increase the chances of survival during travel from the emergency site to a hospital.

A particular concern arises when the emergency personnel have to deal with an unconscious patient or one who cannot communicate. With unconscious patient or patients, who may not be breathing or have other substantial risks of death, the emergency personnel treating the non responsive patient are unable to ask the patient about their background or injury of possible causes of their health emergency. In the heat of the moment, while treating an unresponsive patient, and attempting to ascertain why the patient is non-responsive, frequently overlooked is the issue of blood sugar levels which might have caused the patient to become unresponsive. Such frequently occurs in diabetic patients. The same problem can occur with unconscious patients who have ingested drugs or may be having an allergic reaction.

With patients suffering from blood sugar issues, the diagnosis of low or high blood sugar levels in the blood, or with patients where other chemical substance levels in the blood which might cause the patient to be unconscious or unresponsive, such are not always discovered at this earliest stage of treatment when such information could significantly change the course of treatment, and the patient's outcome.

This can occur due to the emergency situation to which the medical provider arrives upon, or in an emergency room when the surroundings are hectic, and where the health care provider is concerned with ascertaining if the patient is breathing, and concurrently trying to place a line into a vein of the patient to provide fluids and/or medication.

This current inability for a quick diagnosis can often further injure the patient when, for example, hyperglycemia or hypoglycemia in a diabetic patient can easily be mistaken as alcohol intoxication or stroke. The patient may be transported without ascertaining or treating the cause of the emergency. Thus, valuable time is lost in treating the actual problem if the reason for a patient's non-responsive state is not ascertained quickly.

As such, there is an unmet need for an intravascular catheter insertion device and method, which concurrent with the positioning of a catheter, provides a means for visually alerting the medical provider, to discerned causes of non-responsive patients which can be achieved from blood analysis. Such a device should be employable concurrent with the insertion of a catheter assembly in the patient, with no extra effort by the user, and concurrently provide the visually discernable alert should blood from the patient have levels of substances past a threshold. Such a device and method should allow a health care provider to quickly and easily view test results, for a range of blood-discoverable disorders, immediately subsequent to the communication of blood from a patient, to the flash chamber of the introducer or angio catheter hub, during the catheter insertion process.

The forgoing examples of related art and limitation related therewith are intended to be illustrative and not exclusive, and they do not imply any limitations on the invention described and claimed herein. Various limitations of the related art will become apparent to those skilled in the art upon a reading and understanding of the specification below and the accompanying drawings.

OBJECTS OF THE INVENTION

It is an object of the present invention to provide a device adapted for use with an intravenous catheter insertion component, which during normal employment thereof is used to place a venous line, and which provides visually discernable feedback to the user, of a concurrent blood analysis.

It is an additional object of this invention for such a visual alert to a patient health problem, such as a colorimetric reagent, to be activated by communication with blood plasma from blood reaching the flash chamber during a catheter insertion, for easy viewing and quick analysis.

It is yet an additional object of this invention to provide and visually discernable blood content analysis device and method which when placed in communication with blood or plasma concurrent with the insertion of a line or catheter, will provide the user with a visually discernable result to the presence of a substance or threshold amount thereof in the blood of the patient being given the line.

These and other objects, features, and advantages of the present invention, as well as the advantages thereof over existing prior art, which will become apparent from the description to follow, are accomplished by the improvements described in this specification and hereinafter described in the following detailed description which fully discloses the invention, but should not be considered as placing limitations thereon.

SUMMARY OF THE INVENTION

In accordance with the purposes of the present invention, as embodied and broadly described herein, the present invention provides a visually discernable warning or result in a component adapted for operative fluid communication with the flash chamber of an introducer for an intravenous catheter into a blood vessel of a patient. The device and method provides a visually discernable alert when blood from the flash chamber of a catheter introducer, or in some modes, a sealed luer lock, communicates with a test component reactive to communicated blood plasma, to visually change. The reaction with the blood or the plasma occurs depending on one or a plurality of reagents positioned therein configured to test for blood contents, substances or threshold high or low levels thereof, to visually change in appearance upon a result.

The device and method may be employed by engaging the reagent testing component to existing introducers in an operative manner, or, it may be practiced through the provision of an introducer having the testing component formed integral or engagable therewith in production as a combination introducer and testing component. This may be with an engageable testing component or employing a testing component as part of the flash chamber components.

The overall object of the device and method herein is the provision of an introducer for a catheter which will employ the blood communicated to the flash chamber, to test for substances carried in, or lacking, or below or above a threshold level, in the blood communicated thereto. Such will occur concurrently with the positioning of the catheter and provide a visually discerned alarm or alert to the user if a tested substance is present, lacking, or present above or below a threshold level for which the blood is concurrently tested during catheter insertion. In another mode, the same testing component can be configured to be engageable with the introducer, or can also be engaged with and employed to receive communicated blood from a sealed leur lock.

The test component, so positioned in operative engagement with an introducer, during use thereof, will provide an immediate visually discernable alert to the user, of a particular patient condition which is discernable using blood or blood plasma and a reactive reagent. The reagent or reagents operatively positioned on the test component can be configured to react and produce a visually discernable alert to the user of conditions of the patient. This can include low or high blood sugar or excessive alcohol levels, opiate levels, or the presence of other chemicals and substances which are discernable using blood plasma communicated to an introducer which has a communicating test component. This is especially helpful to emergency personnel who are confronted with an unconscious or non-responsive patient because a number of causes which may be discerned with a blood analysis, can be confirmed or eliminated concurrent with the insertion of a venous catheter.

During insertion of a catheter with an insertion set, the needle of the introducer in conventional sets, has a distal end which communicates with the flash chamber which extends through the needle hub, and a coaxial catheter. A small point of the introducer needle extends coaxially through the insertable catheter and has a point which extends from the distal end of the catheter.

The testing component if positioned in or in communication with the flash chamber can contain one or more one-way air valves or membranes to allow air to escape as blood enters the flash chamber. The blood communicated to the flash chamber conventionally provides visual confirmation of placement of the needle point and distal end of the catheter into a vein or artery. This signals the user the line is properly placed.

In one mode of the device and method, the rear of a conventional flash chamber, which is conventionally plugged by a microporous plug, can include a visually discernable means of alerting the user to a health condition, such as a colorimetric sheet or layer having a reagent thereon which is reactive to blood or blood plasma contents. Such test sheets are well known in the art and can be employed to test for the presence of a substance or marker therefor or differing levels thereof in the communicated plasma or blood. Such microporous plugs are conventionally positioned in most introducer flash chambers and thus in one mode, employable for the device and method herein, can be adapted using the mode of the device and method herein to include one or a plurality of reagent layers in fluid communication with the flash chamber or the microporous plug, which are visually discernable through the sidewall of the introducer.

In another preferred mode of the component herein, a reactant to blood content levels for certain chemicals and contents is placed in a fluid communication with the flash chamber, using a housing and testing component which may be placed inside, or outside the flash chamber. A pathway for blood flow to the housing is provided axially or through a sidewall of the introducer.

The housing of the engaged or engageable test component, will house material which includes one or a plurality of reagents operatively positioned on sheets or membranes, which are visually reactive to certain blood conditions such as blood sugar levels, alcohol levels, opiate presence or levels, or individual drugs or other substances being present in the patient's blood. Such may be a paper or plastic material with a reactive agent therein which produces a visually discernable change such as a color change upon communication with blood or blood plasma. The paper or plastic material hosting the reagent, as noted, may be placed within the flash chamber, or against a sidewall thereof where it is viewable, or within a sub chamber, or engageable testing component, so long as the reagent contained in the housing, is engaged to achieve a fluid communication with the blood communicated into flash chamber during a catheter insertion.

The testing component as noted may be formed to be removably engageable with the introducer housing to fluidly communicate with the flash chamber to allow the user to engage a testing component having a reagent or reagents operatively positioned therein and adapted to test for one or a plurality of suspected substance levels. Alternatively, it can be engaged at manufacture either axially, or on a sidewall of the housing of the introducer such that it is in a fluid communication with the flash chamber.

In one mode, the visually discernable result or alert can include a colorimetric sheet composed of two layers. A first or outer layer membrane is exposed to blood first and acts as a filter to filter out the red blood cells and pass plasma. A second or inner layer is in communication with the passed plasma and contains one or more reagents which will visually change to a certain color or colors in the presence of an analyte being tested, and can thereby show the presence of a substance or a presence below or above a threshold level.

Small sheets or other types of reagent material may be placed on or against the sidewall of the flash chamber, or within communicating sub chambers of a testing housing engaged or engageable to a fluid communication point with the flash chamber of the introducer. The reagent strips or layer may also be placed in another viewable position so long as the reactive layer is placed in a communication with the fluid within the flash chamber, and provides a result that is visually discernable when viewed by the user.

As blood that enters the flash chamber it concurrently contacts and passes through the filter layer and communicates plasma to contact the colorimetric sheet. Thereafter the reagents within the sheet, will change to a certain color, or sequence of colors, to alert the medical practitioner as to the presence or absence of certain chemicals or materials or substances in the blood, or one or a plurality of threshold levels of such substances within the blood communicated to the flash chamber.

As such, a colorimetric sheet may be placed on a viewable sidewall of the microporous plug per one preferred mode, or in a housing within, or exterior to the flash chamber, or affixed to a wall surface of the flash chamber, or in engaged or engageable component housings or chambers, so that the user can view a visually discernable result such as a color change reaction through the transparent sidewall of the introducer or flash chamber.

The colorimetric sheet should be sufficiently sized and contain the necessary amounts or number of reagents so that a user could discern color changes from chemical reactions with the volume of blood housed communicated from the flash chamber. Additionally, in any of the modes of the device and method herein, the material hosting the reagent, can include a plurality thereof which can be combined to perform several tests at once, and provide multiple viewable results to the user. Further, the colorimetric sheet can be composed of any currently employed substrate material and one or a combination of colorimetric reagents adapted to provide a visual change in appearance upon reacting with one or more elements contained in the blood or plasma.

Additionally, any color reactive material or chemical which will change color or colors in a visually discernable alert to the user, when placed in operative communication with blood or plasma from the flash chamber may be employed if it will react at some threshold level to alert the user visually. Such may be any dry chemicals or gelled chemical or liquid chemical or material which is placed in sub chambers in communication with the flash chamber which will visually react and alert the user.

With respect to the above description, before explaining at least one preferred embodiment of the herein disclosed blood testing invention in detail, it is to be understood that the invention is not limited in its application to the details of construction and to the arrangement of the components in the following description or illustrated in the drawings. The visual alert device adapted for use concurrently with an introducer herein described and disclosed in the various modes and combinations is also capable of other embodiments and of being practiced and carried out in various ways which will be obvious to those skilled in the art. Any such alternative configuration as would occur to those skilled in the art is considered within the scope of this patent. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other catheter insertion devices and blood testing equipment for carrying out the several purposes of the present disclosed device. It is important, therefore, that the claims be regarded as including such equivalent construction and methodology insofar as they do not depart from the spirit and scope of the present invention.

BRIEF DESCRIPTION OF DRAWING FIGURES

The accompanying drawings, which are incorporated herein and form a part of the specification, illustrate some, but not the only nor exclusive examples of embodiments and/or features of the disclosed device. It is intended that the embodiments and figures disclosed herein are to be considered illustrative of the invention herein, rather than limiting in any fashion.

In the drawings.

DETAILED DESCRIPTION OF THE INVENTION

Figure 1:
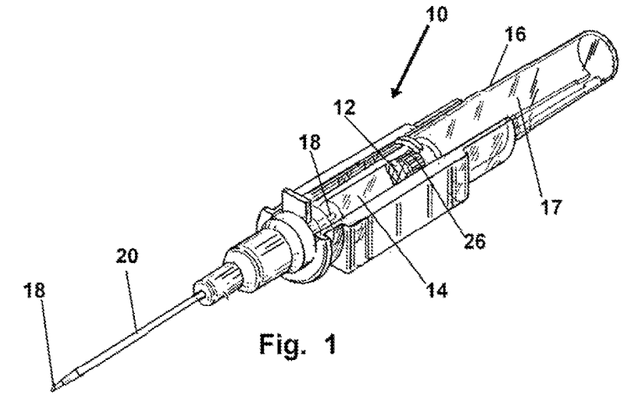
FIG. 1 depicts an isometric view of one mode of the device and method having a microporous plug testing and alert adapted for employment with an introducer during placement of a venous catheter.

Now referring to drawings in FIGS. 1-9, wherein similar components are identified by like reference numerals, there is seen in FIG. 1, the device 10 positioned with the means for substance testing of blood or plasma such as a testing component 12, positioned in direct fluid communication with the flash chamber 14 of a conventional introducer 16. The introducer 16 as conventionally employed, has a needle 18 which extends within the axial passage of a catheter 20 in sealed engagement with a luer lock 22 component. The device 10 and method herein, in all modes includes a testing component 12 having substrate such as a pad or membrane or sheet of material with a reagent or other substance thereon which reacts with substances in the blood in a manner to provide a visually discernable means for alerting the user. Such when viewed by the user will alert them to the presence, non-presence or a threshold low or high level, of that particular substance, chemical, or contents of the blood or blood plasma, which is communicated thereto, and which reacts to such a fluid communication with blood or plasma, such and changes appearance, such as color.

The various modes of the testing component 12 primarily depict a substrate of planar material adapted to the task. However, the substrate is capable of numerous other modes, and any testing component 12 or other component which may be placed in operative fluid communication with a flash chamber 14 of an introducer 16, and which will react in a visually discernable manner to a communication of blood or plasma thereto when a particular substance, chemical, or other element carried in the blood, is considered within the scope of this application.

A colorimetric reagent pad 32 is preferable to determine the concentration of glucose in blood plasma and provide a visually discernable means for the user to view results or an alert. A threshold indication system may be used such that when the concentration is below a predetermined level, the reagent pad 32 remains colorless, and when the concentration goes above that point, a colored dye is activated in the reagent pad 32, and can be detected easily by the human eye.

In a preferred variation, a dual threshold indication system is used such that the reagent pad 32 remains colorless below a predetermined level, changes one color when above the first threshold, and turns a second color when above the second threshold. An example of the dual indication system would be such that the reagent pad 32 is colorless below a glucose concentration of 80 mg/dl indicating low blood sugar, green when between 80 mg/dl and 300 mg/dl indicating normal blood sugar, and dark blue when above 300 mg/dl indicating high blood sugar.

The threshold indication system is accomplished through precise control of the volume of plasma that is able to contact and react on the substrate such as the reagent pad 32, and using precise amounts of scavenger molecules that are consumed before the reaction with the dye is visible. This can either be accomplished by consuming an intermediate reactive species or quickly reacting to turn the dye back to a colorless state once it has reacted with the intermediate reactive species. Once all the scavenger molecules have reacted, reactions can proceed with the dye or the dye is no longer reversed to a colorless state.

In the dual threshold variation, reaction speeds are controlled through enzyme concentrations and the concentration of other reactive species such that the scavenger molecules are reacted before the other two dyes are able to react at an eye-detectable level. The first dye, which is also present in a precisely controlled amount like the scavenger molecules, then reacts before the second dye is able to react at an eye-detectable level. But once all the first dye has reacted, the reaction proceeds onto the second dye.

The reagent pad 32 form of the test substrate, may be created by conventional means in the art such as by dipping a hydrophilic membrane such as filter paper into a solution containing all the starting chemicals and enzymes. Through control of the concentration of chemicals in this solution, and conventional knowledge about how much solution is adsorbed onto the reagent pad 32 during dipping, the amount of starting chemicals can be controlled.

For example, and in no way limiting as to the substance which can be visually discerned using the device 10 and method herein, glucose is first reacted with an enzyme to give rise to a more reactive species that is able to react appropriately with either the scavenger molecules or dyes. In one embodiment, glucose reacts with the enzyme glucose oxidase and oxygen to create gluconic acid and hydrogen peroxide.

Hydrogen peroxide then proceeds to react with a colorless phenolic in the presence of 4-aminoanipyrene (AAP) and the enzyme horseradish peroxidase to create a colored dye and water. This is explained further in U.S. Pat. No. 6,599,474 B2.

There is a wide range of phenolic compounds that can be used, and one that gives a light green color when reacted with AAP is 3-hydroxyquinaldine [2].

To create a threshold visually discernable indication, a reducing agent can be used to convert the colored dye back into a colorless form as shown in reaction. Some possible reducing agents that could participate in reaction include ferrous sulphate and magnesium chloride.

A scavenger compound can also be used to create a threshold indication by consuming the majority of the hydrogen peroxide before it can participate in reaction (2) and indicate the dye. One such compound, 1-cysteine can react directly with hydrogen peroxide.

If may be desirable to control the reaction enzymatically, and ascorbate can be used in conjunction with glutathione to do so for example. An advantage to using enzymatically controlled reactions is that enzyme concentrations can be used to obtain better control over reaction rates.

Note, that because ascorbate is regenerated in such a reaction, the stoichiometrically controlled species for creating a threshold indication is glutathione.

For the secondary threshold indication, hydrogen peroxide reacts with iodine ions and hydrogen ions to create triiodide and water. The triiodide can then form a deep blue complex with starch. Some control over the reaction rate can be achieved by controlling the pH and concentration of iodine ions.

An alternate to using hydrogen peroxide as the reactive species is NADH. This is described in U.S. Pat. No. 5,200,325. Glucose reacts with NAD+ and the enzyme glucose dehydrogenase to create NADH and gluconolactone. The NADH is the reactive species that continues on to the next reactions.

Pyruvate can be used as a scavenger to stop any activation of a dye below a specified threshold of glucose. The conversion of the lactate into acetate ensures that the lactate does not undergo a reverse reaction or involve itself in any side reactions.

Once all the pyruvate is consumed, the NADH can proceed to react with an indicator in the pad. In the presence of lipoamide dehydrogenase, NADH can react with lipoamide (LA) to create a reduced form of lipoamide.

The reduced form of lipoamide can react with various disulfide indicators to create color. For example, 2,2'-dithiobis(pyridine-N-oxide) (DTPO) may be employed. The reduced form of the disulfide indicator produces color. The amount of LA and DTPO can be precisely controlled along with the amount of lipoamide dehydrogenase enzyme to have all the DTPO and LA be in a reduced state at a desired threshold concentration of glucose. Once all the DTPO and LA are in a reduced state, a second threshold reaction can become the primary indication. In this case the NADH can proceed to react with 2-(p-iodophenyDJ-(p-nitrophenyl)-5-phenyltetrazolium chloride (INT) in the presence of the enzyme diaphorase to create NAD+ and formazan, the colored indicator and reduced form of INT.

This is an example of a dual threshold color indication using NADH as the reactive species. The colors of the specific indicators used in this example may not be optimized for this application, but it is expected that there are multiple colors that can be produced with similar molecules to the ones used. The reagent pad 32 or testing substrate, can be formed to be ethanol sensitive by changing glucose oxidase to alcohol oxidase in the first reaction noted above which generates hydrogen peroxide. Similarly, glucose dehydrogenase can be replaced with alcohol dehydrogenase which generates NADH in reaction. The rest of the chemistry should proceed similar to above.

The aforementioned are simply examples of modes of enabling the device 10 with a reagent pad 32 which after a duration of time of exposure to communicated blood plasma, will visually react to the presence of a substance or analytes thereof in the blood plasma, or to analytes of a substance or the substance itself above a threshold level. The employed testing substrate such as depicted reagent pad 32 can be segmented to multiple zones to include multiple reactions to the communicated plasma, to provide multiple individual visually discernable alerts for respective multiple individual substances present, and/or above or below threshold levels by volume.

As depicted in FIG. 1, a conventional catheter 20 insertion device such as an introducer 16 is equipped with some form of colorimetric-enabled testing component 12 having a substrate such as the shown reagent pad 32 which will visually change in appearance if a substance such as chemical, drug, or other element or substance in the blood communicated to it, is present, or present at above or below a threshold level. Shown in the modes of FIGS. 1-9, a conventional introducer 16 includes a tubular housing 17 defining a body and reservoir for the flash chamber which has a hollow needle 18 extending therefrom though the axial passage in the catheter 20. An axial conduit communicating through the needle at both ends, is in an operative sealed communication with the formed flash chamber 14 in the housing 17, which is formed of substantially transparent material such that the interior of the flash chamber 14 is viewable through the sidewall surrounding it.

In all modes of the device 10 where the needle 18 is coaxial to the catheter 20, the point of the needle 18 is seen to extend from the distal tip of the catheter 20, which is mounted on the luer lock 22 component. This allows the needle 18 to be inserted through the flesh of the patient and be positioned within the desired vein or artery.

Upon a proper communication of the distal end of the needle 18 with the interior of a vein or artery, blood immediately flows through the axial conduit of the needle 18 and into the flash chamber 14 thereby signifying proper positioning. The flash chamber 26 on conventional introducers 16 can contain one or more one-way air valves, or membranes, to vent or allow air to escape as blood enters. Conventionally one such air passage is provided by a flash plug 26.

As shown in FIG. 1, at the rear of many conventional flash chambers 14 in conventional introducers 16, is located a microporous plug 26. In one preferred mode of the device 10 herein, as for instance in FIGS. 1 and 8-9, the testing component 12 or another means for producing a visually discernable alert, upon communication with blood or plasma in the flash chamber 14 which has a particular content or threshold level of a particular analyte for a substance or the substance itself, may be barrel-shaped or the testing substrate may be positioned on, or formed as part of, the flash plug 26 in a position where it is viewable through a wall of the introducer body.

Figure 2:
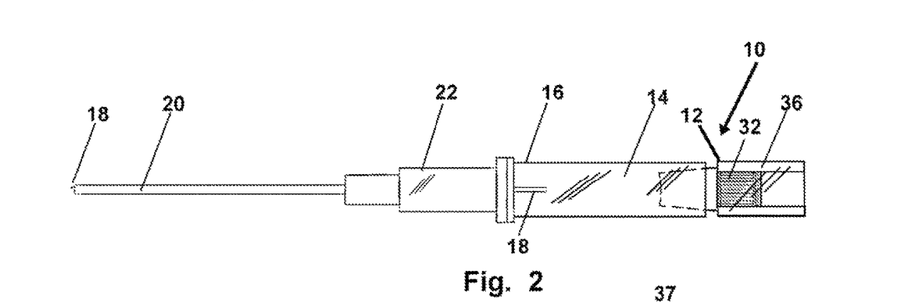
FIG. 2 shows a side view of the device and method herein wherein a test component is adapted for sealed engagement with a proximal end of an introducer in operative fluid communication with the flash chamber thereof.
Figure 3:
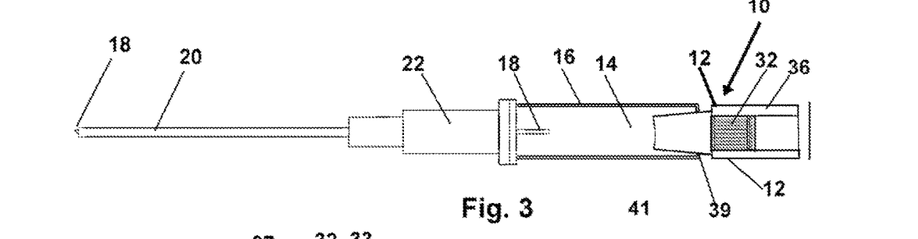
FIG. 3 depicts a sectional view of the device of FIG. 2.
Figure 4:
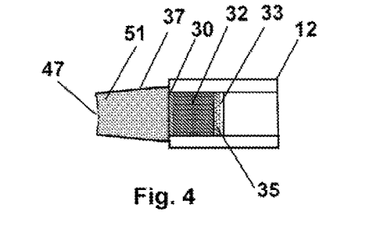
FIG. 4 shows a mode of the device and method herein wherein the device is configured as a removably engageable test component adapted for operative engagement with the introducer and flash chamber of an introducer.
Figure 4A:
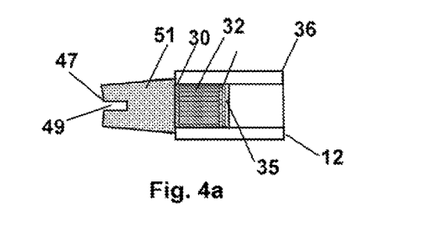
FIG. 4*a* shows the device of FIG. 4 also having a slot adapted for engagement with an electronic blood testing component.

In another preferred mode of the device 10 per FIGS. 2-4 the means for producing a visually discernable alert or test result for the user, to a blood content of a particular substance analyte, marker, or the substance itself, over or under a threshold level, shown as a testing component 12, using an appropriate substrate material which is formed in an engaged or engageable barrel or circular shape for example as shown in FIGS. 4 and 4a.

In operation herein, in all modes where a testing component 12 is employed, blood from the flash chamber 14 is communicated to the testing component 12. During such communication to the testing substrate, plasma is separated from the whole blood using a plasma separation membrane 30 (FIGS. 4-4a and 8-9 for example) such as that available from Pall Corporation for example. The plasma separation membrane 30 prevents red blood cells from coming in contact with the reagent pad 32 and distorting the color. The plasma will be able to wick through the plasma separation membrane 30 (PSM) while the red blood cells are left behind. A similar membrane 30 is described in U.S. Pat. No. 5,972,294, and an example currently available for sale is VIVID Plasma Separation Membrane by Pall Corporation.

Red blood cells have an approximate diameter of 6.2-8.2 µm and by using an asymmetric membrane 30 where the pore size varies in a gradient starting on the receiving side from values such as 50 µm to 0.1 µm, red blood cells will be trapped in the receiving side of membrane. The membrane itself is made of a hydrophilic material that will readily soak up and wick plasma, so the red blood cells are trapped on the receiving side of the membrane while the plasma is wicked to the opposite end. This ensures that only plasma will soak into the reagent pad.

In one preferred mode of the device 10, it is desired to induce a blood clot between the blood in the flash chamber 14 and that which is communicated through the plasma separation membrane 30 to the test substrate as a means for limiting the volume of fluid communicated through the membrane 30, and then to the reagent pad 32, to stop an excess communication and a continuous diffusion of glucose for example which can cause a testing error.

Means to induce clotting on or in the membrane 30 such as by causing blood clots, may be induced by several different compounds. Potassium ferrate is one used in U.S. Pat. No. 6,187,347 B1, and kaolin and zeolite are used in US patent application US20090299253 A1. Blood has a natural clotting cascade to seal up wounds to the body, and it may be desired to induce and accelerate clotting to seal up the plasma separation membrane 30 in instances where the testing being done requires a certain volume of fluid communicated to the substrate having the visually discernable test results thereon to be accurate.

The clotting speed, and therefor the volume of plasma or fluid passed through the membrane 30, may be tightly controlled by varying the amount of the clotting agent on, adjacent to, or within the separation membrane 30, to allow plasma flow before clotting only for a sufficient time for a determined volume of blood plasma to communicate through the plasma separation membrane 30, and thereby stop glucose diffusion in the testing component, beyond that point in time where the volume of plasma passes through.

An alternative, described in patent application WO2010062734 is using chitosan, which does not induce the full clotting cascade, but only forms a localized clot. It may be desirable to pattern the chitosan in such a way on the plasma separation membrane 30, such that there is not 100% coverage initially, but after contact with the blood and subsequent wicking through the plasma separation membrane, all contact of blood to the plasma separation membrane 30 has ceased after the desired amount has been absorbed. In a preferred embodiment, a chitosan gel or solution is cast or sprayed directly on the plasma separation membrane and dried, forming a layer. The chitosan matrix molecular weight and thickness is tightly controlled to allow a precise amount of plasma through the plasma separation membrane before being sealed.

Thereafter, the plasma wicks from the plasma separation membrane 30 and fluidly communicates with the substrate providing the visually discernable outcome to the test component 12 such as the reagent pad 32. The reagent pad 32 may be configured in any manner of conventional ways to produce a visually discernable alert, such as a color or color change, when a threshold level of a substance analyte or the substance itself being tested-for, is discerned. The reagent pad 32 may remain the original color if the agent or material being tested for is not present in the plasma, or if it is present below a specified concentration. If the concentration is above the specified level, the reagent pad 32 will have a colored change indication detectable by the human eye.

Shown in FIGS. 2 and 3, the testing component 12 is positioned to be in a fluid communication with blood communicated thereto, at the rear of the flash chamber 14, in place of the plug of FIG. 1. As depicted, the substrate employed as the testing component 12 is positioned within a substrate housing of a tubular or barrel shape and has a blood communication and testing system within such as those of FIGS. 4-4a. Also, in this mode, the testing component 12, might be one of a plurality of substrates which are positioned in differing engageable testing components 12 available for such testing, and engaged with a reagent housing 36 which is configured for a sealed engagement with the housing 17 of the introducer 16. This engagement is by cooperative fasteners formed or positioned on each, and may be a threaded engagement 37, which places the testing component 12 such that the substrate or substrates providing the visually discernable result to fluid communication with the flash chamber 14, or may be a frictional engagement achieved when a tapered first end is engaged in an aperture at the rear of the housing 17 of the introducer 16.

This engageable configuration would allow the employment of a kit of testing components 12 such as in FIGS. 2-4a, with each configured with one or more substrates within a substrate housing, with proper chemical reagents imparted or positioned thereon, to produce a visually discernable alert, to the presence of a different particular chemical, component, or substance in the blood. Thus the user could pick one engageable testing component 12 from the plurality in the kit thereof, and employ it during an introduction of a catheter on a patient, to test for a particular substance during insertion. It should be noted that the tapered first end shown for the testing component 12 of FIGS. 2-4a, may also be employed to engage with a sealed leur lock of a catheter already placed in a patient, to perform a quick test for blood levels of particular substances to which the testing component 12 is configured to react. The tapered portion will engage in the aperture of the luer lock and open it temporarily for fluid communication to the substrate within the substrate housing of the test component 12.

In FIGS. 4 and 4a, can be seen sectional views of the axial-engageable mode of the testing component 12. While shown in a frictional engagement of the tapered first end of the housing wall 37, which is adapted to engage an aperture 39 through the housing 17 of the introducer 16, a threaded twisting engagement through the aperture 39 (not shown but well known) could also be employed, or mating cooperative fasteners on both the housing of the introducer 16 and the testing component 12 being attached.

As shown in FIGS. 4-4a, a wall 37 forms the exterior of the substrate or reagent housing 36 and is tapered at a first end which has an aperture 47 providing fluid communication to the substrate positioned within the interior of the substrate or reagent housing 36. A wicking material 51 or plasma separation membrane 30, depending on construction, receives blood in the fluid communication from the flash chamber when operatively engaged such as in FIG. 3.

Blood is communicated to the blood to a plasma separation membrane 30 which filters the red cells and passes blood plasma to the test substrate shown in this mode as reagent pad 32. Also shown in FIG. 4a, is a recess 49 formed into the wall 37 of the housing 36 on both sides extending from the edge of the aperture 47. This recess 49 extends traverse to the center axis of the housing 36 such that an elongated conventional blood test strip (not shown) used to test blood for substances, can be engaged within the recess 49 and drops of blood absorbed by the wicking material 51 can be communicated to the test strip, to test for a blood born substance if such is not being tested for by the device 10. Currently, users of introducers use blood which drips from the sharp needle, at great risk to a puncture wound to themselves, to accomplish the transfer of patient blood to a test strip.

Plasma communicating to and through the reagent pad 32 will communicate through a moisture indicator layer 33 and thereafter cease further communication rearward once it encounters the backing layer 35 which is configured to pass air from the flash chamber 14 to the atmosphere but block the larger fluid molecules from exit. The backing layer 35 thus provides means for venting air from the flash chamber 14 to allow blood and plasma to fill it.

The reagent pad 32 or substrate, as noted herein, in all modes of the device 10 such as of FIG. 1, 2-4a, or 5-7, will be imparted with appropriate reactive substances to visually react to a determined substance in the blood plasma, and change in appearance and provide a visual alert to the user, of the presence or lack of presence of a substance in the blood of the patient. This can be seen through the sidewall of the introducer housing 17, or the housing of the engaged or engageable testing component 12, no matter the location or means of engagement with the introducer 16.

Figure 5:
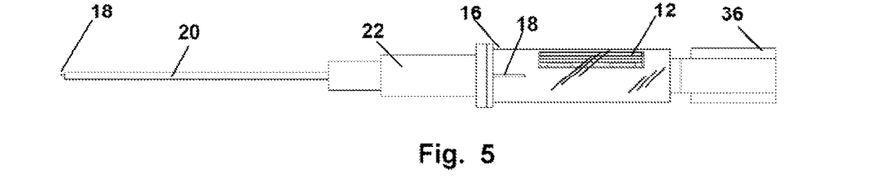
FIG. 5 depicts another mode of the device herein showing an internal or integral construction reagent housing which yields the visual report or alarm on communication with blood or plasma.
Figure 6:
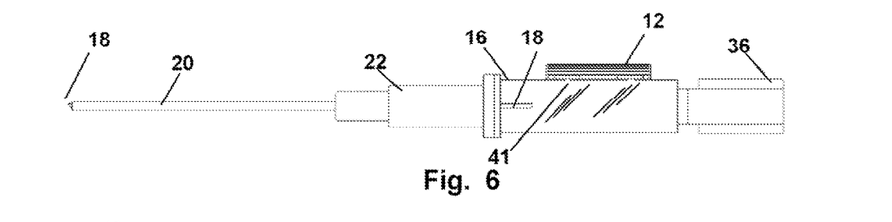
FIG. 6 depicts a mode of the device positioned in a housing in operative engagement on the exterior of an introducer and in operative communication with the flash chamber.
Figure 7:
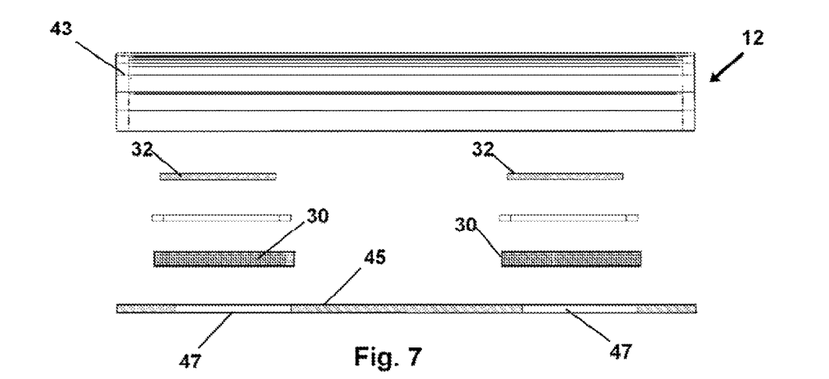
FIG. 7 shows an exploded view of the introducer-engaged housing for the reagent layer or layers.

As shown in FIGS. 5-7 the testing component 12 can be elongated or planar in configuration, and be engaged to the interior of the flash chamber as in FIG. 14, or the exterior of the flash chamber 14 as in FIG. 5 or be formed integral with the walls defining the introducer 16 or flash chamber 14. In either mode, a passage 41 will be operatively be positioned to communicate blood from the flash chamber 14, to the one or a plurality of substrates such as reagent pads 32 shown for instance in FIG. 7 in the exploded view of this mode of the device 10.

A transparent wall or cover 43 is placed in sealed engagement with a base 45, (which may be the wall forming the flash chamber 14) and one or a plurality of apertures 47 will communicate with passages 41 providing fluid communication with the flash chamber 14. This mode can be formed integral to the housing 17, or engaged on the exterior thereto using adhesive or other means to engage the base 45 or the cover 43 to a wall of the housing 17. Or, as noted, if manufactured, it may be formed integral to the wall defining the flash chamber 14 or introducer 16.

In all modes of the device 10 the testing component 12 can include substrate adapted with appropriate test material to produce a threshold visually discernable alert, which may have one, or a plurality of concurrent different visually discernable results possible. As shown in FIG. 7, the testing component 12 includes the separation membrane 30 which communicates the plasma to the exterior which has a plurality of sections formed thereon, with each section providing a differing visually discernable alert, such as colors, to the user showing the presence in the blood tested of the particular component, chemical, or substance in the blood at a particular level. For example the reagent pad 32 of one section, can remain colorless below a specified concentration, and in a second section as shown, there may be an alert for another tested substance being present in the blood or a different level of the first component tested.

Figure 8:
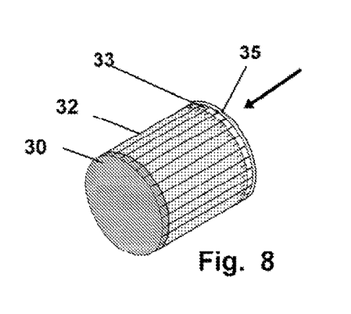
FIG. 8 shows a mode of the device having a circular configuration such as would be employed as the microporous plug in the depiction of FIG. 1.
Figure 9:
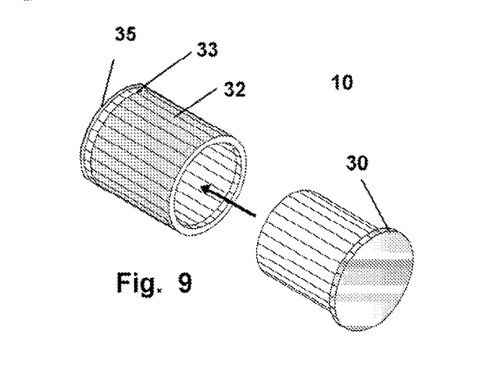
FIG. 9 depicts the device of FIG. 8 in an exploded view.

As shown in FIGS. 8-9 the testing component 12 providing the visually discernable alert or alerts, may be cylindrical such as when employed as the flash plug 26 in a conventional introducer 16. In this mode, the separation membrane 30 communicates plasma therethrough to the reagent pad 32 or pads, which will then visually provide a result or alert concerning the level or presence of a substance in the sampled blood. Plasma will also communicate through a moisture indicator layer 33 which in all modes changes appearance to signify moisture communication thereto, and thereafter cease further communication rearward once it encounters the backing layer 35 which is configured to pass air from the flash chamber 14.

Particularly preferred in any mode of the device 10 when used in an operative engagement with an introducer 16 would be a colorimetric blood glucose or ethanol test, using a substrate such as the reagent pad 32 configured to provide a visually discernable alert, when blood glucose or ethanol concentration is beyond a predetermined point whereby the reagent pad 32 reacts in a manner to provide a visually discernable alert or result.

However, any substance or level thereof in the blood may be tested and a visually discernable alert produced using the appropriate reagents which react to the presence of a substance or marker for such in the blood. This provides the medical provider with valuable information concurrent with the introduction of the catheter to the patient with no extra effort or time.

Any of the catheter components as described above can be produced from any of the standard disposable and non-toxic plastics or metals used with other intravenous catheters. The color indicator providing a visually discernable alert to the user for the substance or level of substance in the blood communicated to a flash chamber 14 may be any material which will react to such substances in the blood and provide the visual alert which as known to those skilled in the art may be any of thousands of potential tests and resulting visually discernable reactions.

In a method of use of the device 10 herein, a user will employ an introducer 16 to place a catheter in the vein of a patient. In a first step, if the introducer 16 is pre-configured with a testing component 12 in communication with the flash chamber 14 of the introducer 16, the user will pierce the vein of the patient and discern if blood is communicated to the flash chamber 14. Subsequent to such communication to the chamber 14, the user will view the reagent pad 32 within the testing component 12 to ascertain if a visually discernable alarm or result has been found.

If employing an introducer 16 without a pre-mounted testing component 12, the user will choose a testing component 12 from a group which will provide a desired visual alarm to the presence of a substance or level thereof once blood from the flash chamber 14 reaches it. The user will engage the testing component 12 into an aperture of the introducer 16 which is configured to communicate plasma to the testing component 12. Thereafter the user will engage the needle of the introducer 16 with the vein of a patient, whereby blood will communicate to the flash chamber 14, and cause the substrate or reagent pad 32 of the chosen testing component 12 engaged, to react and either provide a visually discernable alarm or result to the user if the substance being tested for is present or is present at a level above a threshold.

As noted, any of the different configurations and components can be employed with any other configuration or component shown and described herein. Additionally, while the present invention has been described herein with reference to particular embodiments thereof and steps in the method of production, a latitude of modifications, various changes and substitutions are intended in the foregoing disclosures, it will be appreciated that in some instance some features, or configurations, or steps in formation of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

Further, the purpose of any abstract of this specification is to enable the U.S. Patent and Trademark Office, the public generally, and especially the scientists, engineers, and practitioners in the art who are not familiar with patent or legal terms or phraseology, to determine quickly from a cursory inspection the nature and essence of the technical disclosure of the application. Any such abstract is neither intended to define the invention of the application, which is measured by the claims, nor is it intended to be limiting, as to the scope of the invention in any way.

What is claimed is:

1. A test component for blood, comprising:
    an introducer for the introduction of a catheter into a vein or artery of a patient, said introducer having a housing that defines a flash chamber, and a needle in communication with the flash chamber;
    a substrate configured to generate a visually discernable reaction to the presence or a threshold level of a substance in said blood; and
    a fluid communication pathway between said substrate and said flash chamber, said fluid communication pathway defined by a surrounding sidewall of said housing of said introducer;
    said substrate generating said visually discernable reaction viewable subsequent to a fluid communication of a portion of said blood from said flash chamber to said substrate via said fluid communication pathway.

2. The test component for blood of claim 1, additionally comprising:
    a separation membrane interposed in said fluid communication pathway between said flash chamber and said substrate;
    said separation membrane configured to allow only blood plasma from said portion of blood to pass through said fluid communication pathway.

3. The test component for blood of claim 2, additionally comprising:
    a microporous membrane positioned within said flash chamber;
    said microporous membrane defining said separation membrane; and
    said substrate positioned on or adjacent to a surface of said microporous membrane viewable through said sidewall of said housing of said introducer.

4. The test component for blood of claim 3, additionally comprising:
    a clotting factor on or adjacent to said separation membrane, to clot said blood at said separation membrane.

5. The test component for blood of claim 2, additionally comprising:
    said substrate positioned within a chamber of a substrate housing which is engageable with said housing of said introducer; and
    said fluid communication to said substrate communicating from said housing of said introducer to said chamber of said substrate housing.

6. The test component for blood of claim 5, additionally comprising:
    a clotting factor on or adjacent to said separation membrane, to clot said blood at said separation membrane.

7. The test component for blood of claim 2, additionally comprising:
    a clotting factor on or adjacent to said separation membrane, to clot said blood at said separation membrane.

8. The test component for blood of claim 1, additionally comprising:
    a microporous membrane positioned within said flash chamber; and
    said substrate positioned on or adjacent to a surface of said microporous membrane which is viewable through said sidewall of said housing of said introducer.

9. The test component for blood of claim 1, additionally comprising:
    said substrate positioned within a chamber of a substrate housing which is engageable with said housing of said introducer; and
    said fluid communication to said substrate communicating from said housing of said introducer to said chamber of said substrate housing.

10. A method of testing a patient's blood for a substance comprising the steps of:
    providing a test component for blood comprising:
        an introducer for the introduction of a catheter into a vein or artery of a patient, said introducer having a housing that defines a flash chamber, and a needle in communication with the flash chamber;
        a substrate configured to generate a visually discernable reaction to the presence or a threshold level of a substance in said blood; and
        a fluid communication pathway between said substrate and said flash chamber, said fluid communication pathway defined by a surrounding sidewall of said housing of said introducer;
        said substrate generating said visually discernable reaction viewable subsequent to a fluid communication of a portion of said blood from said flash chamber to said substrate via said fluid communication pathway;
    puncturing the vein or artery of said patient with said needle engaged to said introducer;
    allowing blood from said vein or artery to communicate axially through said needle to said flash chamber in said introducer;
    allowing a portion of said blood to fluidly communicate with said substrate; and
    viewing said substrate to ascertain said visually discernable reaction.

* * * * *